United States Patent [19]

Tumangday

[11] 4,053,053
[45] Oct. 11, 1977

[54] VENIPUNCTURE AID DEVICE

[75] Inventor: Fidel G. Tumangday, Los Angeles, Calif.

[73] Assignee: The Raymond Lee Organization, Inc., New York, N.Y. ; a part interest

[21] Appl. No.: 680,282

[22] Filed: Apr. 26, 1976

[51] Int. Cl.² .................. B65D 85/00; A61F 15/00
[52] U.S. Cl. ................................. 206/441; 206/229
[58] Field of Search ............... 206/441, 440, 438, 223, 206/229, 210, 361

[56] References Cited

U.S. PATENT DOCUMENTS

| | | | |
|---|---|---|---|
| 2,952,354 | 9/1960 | Whitelaw et al. | 206/440 |
| 3,388,702 | 6/1968 | Steel | 206/440 |

*Primary Examiner*—William T. Dixson, Jr.
*Attorney, Agent, or Firm*—Daniel Jay Tick

[57] ABSTRACT

A bandage strip has a central area and two side areas each on a corresponding side of the central area and each having pressure adhesive thereon. The bandage strip has a cotton pad affixed to the central area and extending beyond the plane of the bandage strip. A pair of strips of protective material are each removably affixed to a corresponding one of the adhesive covered sides and extend over half the cotton pad. An alcohol swab rests on one of the strips of protective material. A cotton pad rests on the other of the strips of protective material. Additional protective material releasably antiseptically encloses the bandage strip, alcohol swab and cotton pad.

1 Claim, 4 Drawing Figures

U.S. Patent     Oct. 11, 1977     4,053,053
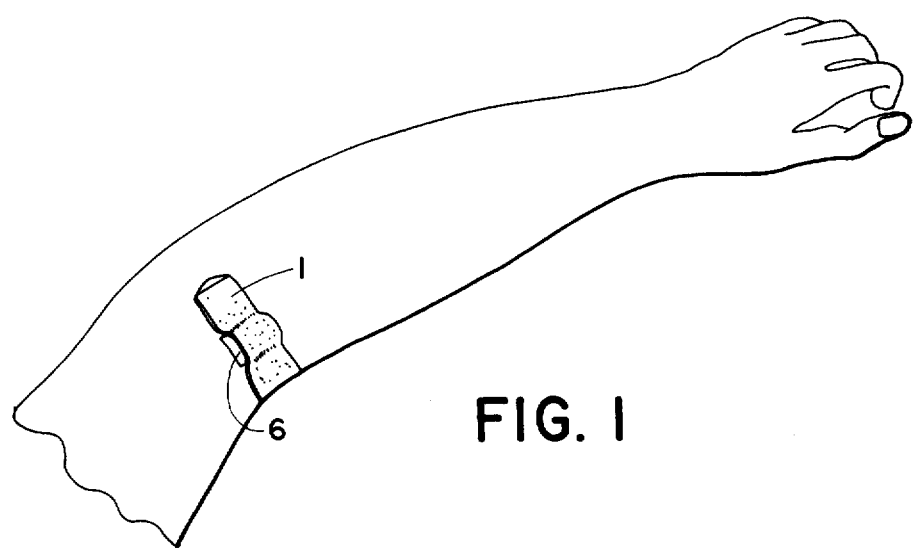
FIG. 1
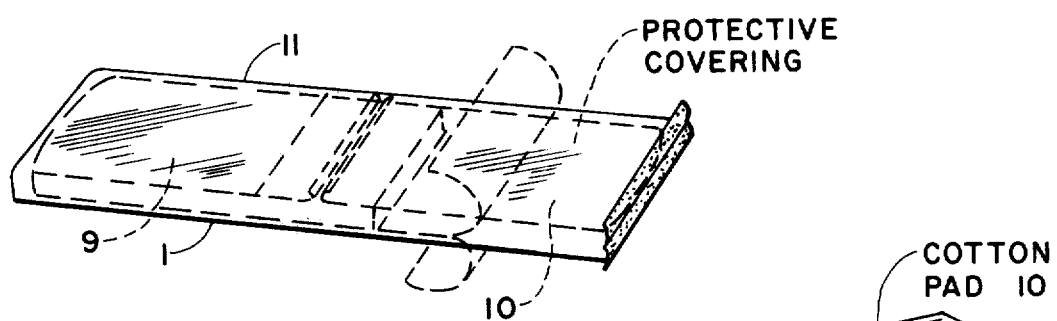
FIG. 2
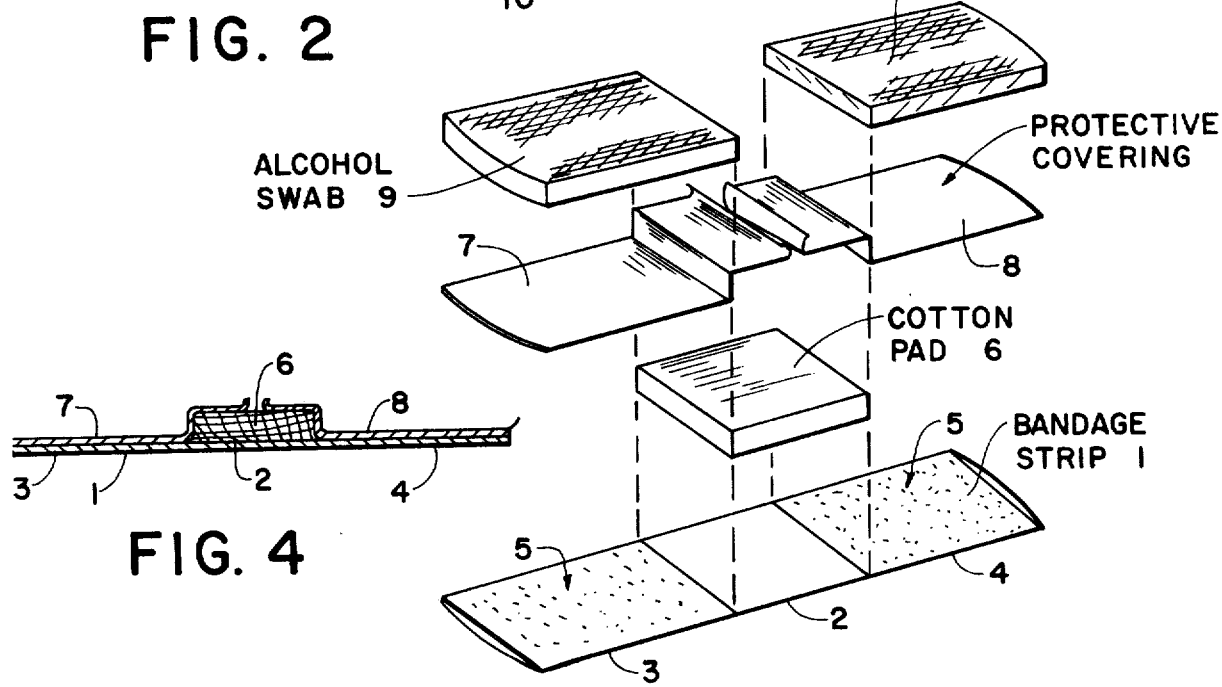
FIG. 4
FIG. 3

VENIPUNCTURE AID DEVICE

BACKGROUND OF THE INVENTION

The present invention relates to a venipuncture aid device.

Objects of the invention are to provide a venipuncture aid device of simple structure, which is inexpensive in manufacture, used with facility and convenience by anyone, with or without medical training, and functions to provide immediate and effective items for stopping bleeding from a venipuncture wound immediately and for preparing a person for the insertion of a needle into a vein.

BRIEF DESCRIPTION OF THE DRAWINGS

In order that the invention may be readily carried into effect, it will now be described with reference to the accompanying drawings, wherein:

FIG. 1 is a view of part of an embodiment of the venipuncture aid device of the invention in use;

FIG. 2 is a perspective view of an embodiment of the venipuncture aid device of the invention prior to unwrapping;

FIG. 3 is an exploded view of an embodiment of the venipuncture aid device of the invention; and FIG. 4 is a cross-sectional view of part of the venipuncture aid device of the invention.

DETAILED DESCRIPTION OF THE INVENTION

The venipuncture aid device of the invention comprises a bandage strip 1 having a central area 2 and two side areas 3 and 4 (FIGS. 3 and 4) each on a corresponding side of the central area and each having pressure adhesive 5 thereon (FIG. 3). The bandage strip 1 has a cotton pad 6 (FIGS. 1, 3 and 4) affixed to the central area 2 and extending beyond the plane of the bandage strip, as shown in the FIGS.

A pair of strips of protective material 7 and 8 (FIGS. 3 and 4) are each removably affixed to a corresponding one of the adhesive covered sides 3 and 4, respectively, and extend over half the cotton pad 6.

An alcohol swab 9 rests on the strip of protective material 7 (FIGS. 2 and 3).

A cotton pad 10 rests on the strip of protective material 8 (FIGS. 2 and 3).

Additional protective material 11 (FIG. 2) releasably antiseptically encloses the bandage strip 1, the alcohol swab 9 and the cotton pad 10. In other words, the venipuncture aid device of the invention is antiseptically wrapped in a package of additional protective material 11.

While the invention has been described by means of a specific example and in a specific embodiment, I do not wish to be limited thereto, for obvious modifications will occur to those skilled in the art without departing from the spirit and scope of the invention.

I claim:

1. A venipuncture aid device, comprising
   a bandage strip having a central area and two side areas each on a corresponding side of the central area and each having pressure adhesive thereon, said bandage strip having a cotton pad affixed to the central area and extending beyond the plane of the bandage strip;
   a pair of strips of protective material each removably affixed to a corresponding one of the adhesive covered sides and extending over half the cotton pad;
   an alcohol swab on one of the strips of protective material;
   a cotton pad on the other of the strips of protective material; and
   additional protective material releasably antiseptically enclosing the bandage strip, alcohol swab and cotton pad.

* * * * *